US00PP08961P

United States Patent [19]

Klemm

[11] Patent Number: Plant 8,961

[45] Date of Patent: Oct. 25, 1994

[54] GERANIUM NAMED KLEGREO

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 172,618

[22] Filed: Dec. 23, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its compact growth, very round and strong umbels with long lasting flowers of a dark pink color having abundant dark foliage.

1 Drawing Sheet

BACKGROUND OF THE NEW PLANT

The present invention comprises a new and distinct cultivar of geranium, botanically known as *Pelargonium zonale*-Hybride. The parents of this new cultivar are unknown. Sometimes when we take a seed from the mother plants, a seed is sometimes lost and falls in the soil and when the seed is found the parents are unknown. This is what happened with the claimed cultivar. The present cultivar was discovered in 1989 in Stuttgart, Germany and has been repeatedly asexually reproduced by cuttings in Stuttgart, Germany and Teneriffe, Italy over a four-year period. It has been found to retain its distinctive characteristics through successive propagations and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to the R.H.S. Colour Chart of The Royal Horticultural Society of London.

THE PLANT

Classification:

*Botanical.*—*Pelargonium zonale*-Hybride.

*Commercial.*—Zonal geranium.

Parentage:

*Seed parent.*—Unknown.

*Pollen parent.*—Unknown.

Form: Compact growing bush.

Shape: Round and low.

Height: About 150 mm in April and about 250 mm in September.

Stem length: Approximately 60 mm.

Number of stems per stalk: Approximately 4–5 from May until the end of September.

Number of stalks per plant: Approximately 15 in October.

Internode length: About 10–mm depending on the light where the plant is propagated.

Growth rate: Upright and vigorous. The time from propagation to the time of sale is approximately 77 days.

Strength: Very good.

Branching character: Very good branching.

Foliage:

*Quantity.*—Many robust leaves.

*Size.*—About 60×70 mm.

*Shape.*—Kidney-shaped.

*Margin.*—Bicrenate.

*Texture.*—Smooth.

*Zonation.*—The leaves have some zonation. The zonation becomes more conspicuous when the plant is outside on a cold night. Therefore, in May and September, when the temperature at night tends to be cooler, the plant exhibits better zonation.

Ribs and veins: None.

Color: Upper side: Dark Green — RHS 147-A. Under side: Light Green — RHS 146-A.

Length of leaf stem: About 30–40 mm.

THE BUD

Size: Medium.

*Diameter.*—About 8 mm.

*Length.*—About 9 mm.

*Depth.*—About 12 mm.

Shape: Elliptical.

Form: Ovoid and pointed.

Rate of opening: Slow to medium.

Color: When sepals first divide: Light pink — RHS 47-D. When petals begin to unfurl: dark pink — RHS 46-D.

Sepals:

*Number.*—5.

*Shape.*—Long and pointed.

*Color.*—Inside — green — RHS 146-A. Outside — green — RHS 146A.

*Form.*—Standing up.

Petiole of florets:

*Length.*—About 23 mm.

*Strength.*—Very strong. Klegreo grows erect. The florets are arranged hemispherically around the center of the cluster. The floret is medium to large in size — approximately 46×46 mm.

*Color.*—Dark green — RHS 146-B.

THE FLOWER

Blooming habit: Continuous and profusely from April until October.

Size: Medium to large. Approximately 46 mm in diameter and 4 mm deep.

Borne: Singly in a cluster.

*Form.*—Cup.

Changes of the form with maturity: The cup becomes a little more flat.

Petals:

*Number.*—About 8-10 per floret.

*Arrangement.*—Imbricated.

*Margin type.*—Entire.

*Form.*—Very broad.

*Color.*—Outer petal: The body is RHS 46-D in color. The reverse side is RHS 47-D in color. The base is RHS 46-D in color. Inside petal: The body is 46-D in color. Reverse side: RHS 52-C in color.

*Pattern.*—The petals express a pattern which includes a darker red-violet blush-like spot in the central part of the petal which effuses or bleeds into the predominant dark pink color of the top surface. On the two-upper petals the spot is separated from the attachment point of the petal by a very light pink basal zone, except for the veins, which have the color of the spot. These markings may be wholly or partly masked be the overlying petaloids which do not express similar color markings.

Texture: Soft.

Appearance: Satiny.

How long do petals remain on stem: About six days depending on the weather.

Petaloids:

*Number.*—About 1 to 3.

*Size.*—About 4-6 mm.

*Color.*—Dark pink — RHS 46-D.

Persistence: Matured florets or clusters should be picked off.

Disease resistance: Klegreo is rather robust against Botrytis.

Weather resistance: Klegreo is not unusually affected by wet or hot weather.

Lasting quality:

*On living plant in pot.*—About 25-28 days.

*As a cut flower.*—About 7 days.

Fragrance: No perceptible fragrance.

REPRODUCTIVE ORGANS

Stamens:

*Anthers.*—Approximately 6-7 positioned around the ovaries about 2.0 mm in length.

*Filaments.*—about 6 mm in length and light pink in color.

Pollen: Yellow-orange in color.

Pistils:

*Number.*—One.

*Length.*—Approximately 7 mm.

*Stigmas.*—Pink to red in color.

Ovaries: Green in color.

Seed: Fertile.

*Shape.*—Ovoid.

*Color at maturity.*—Brown.

I claim:

1. A new and distinct geranium cultivar substantially as herein shown and described, particularly distinguished by its compact growth and very round and strong umbels with long lasting flowers of a dark pink color, having abundant dark foliage.

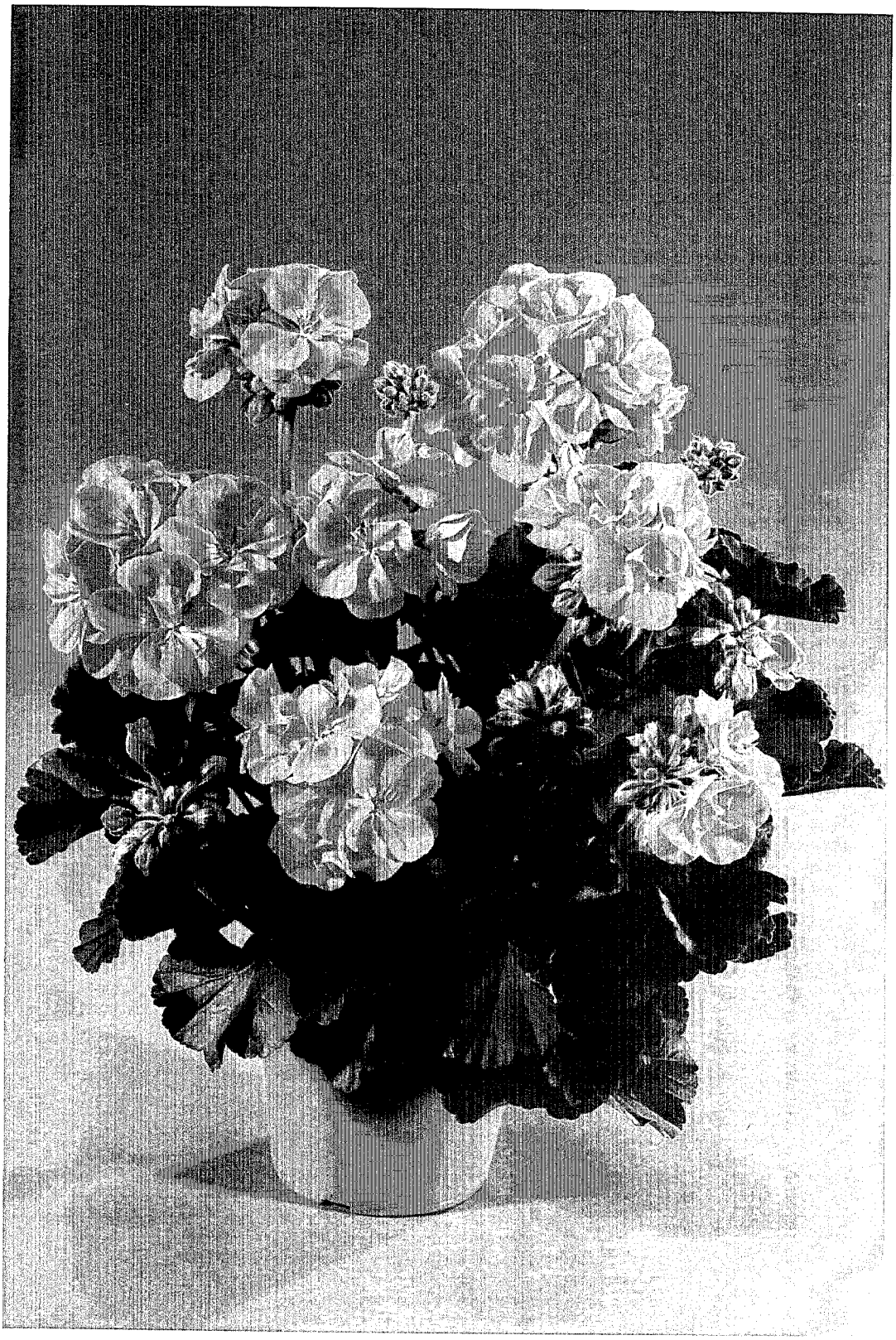

* * * * *